United States Patent
Jernelius et al.

(10) Patent No.: US 12,005,043 B2
(45) Date of Patent: *Jun. 11, 2024

(54) FORMULATIONS OF AG10

(71) Applicant: EIDOS THERAPEUTICS, INC., San Francisco, CA (US)

(72) Inventors: Jesper Jernelius, San Francisco, CA (US); Mark Michael Menning, San Francisco, CA (US)

(73) Assignee: EIDOS THERAPEUTICS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,479

(22) Filed: Jan. 18, 2022

(65) Prior Publication Data

US 2022/0313661 A1 Oct. 6, 2022

Related U.S. Application Data

(63) Continuation of application No. 16/542,737, filed on Aug. 16, 2019, now Pat. No. 11,260,047.

(60) Provisional application No. 62/765,154, filed on Aug. 17, 2018.

(51) Int. Cl.
*A61K 31/415* (2006.01)
*A61K 9/20* (2006.01)
*A61K 9/28* (2006.01)

(52) U.S. Cl.
CPC .......... *A61K 31/415* (2013.01); *A61K 9/2009* (2013.01); *A61K 9/2054* (2013.01); *A61K 9/2833* (2013.01)

(58) Field of Classification Search
CPC .................................................. A61K 9/2054
See application file for complete search history.

(56) References Cited

U.S. PATENT DOCUMENTS

| | | | |
|---|---|---|---|
| RE28,819 E | 5/1976 | Thompson | |
| 4,117,149 A | 9/1978 | Bass | |
| 4,232,161 A | 11/1980 | Diana et al. | |
| 4,234,725 A | 11/1980 | Diana et al. | |
| 4,255,329 A | 3/1981 | Ullman | |
| 4,261,928 A | 4/1981 | Diana et al. | |
| 4,328,245 A | 5/1982 | Yu et al. | |
| 4,358,603 A | 11/1982 | Yu | |
| 4,409,239 A | 10/1983 | Yu | |
| 4,410,545 A | 10/1983 | Yu et al. | |
| 4,522,811 A | 6/1985 | Eppstein et al. | |
| 4,657,914 A | 4/1987 | Bernardi et al. | |
| 4,668,640 A | 5/1987 | Wang et al. | |
| 4,764,521 A | 8/1988 | Herron | |
| 5,315,015 A | 5/1994 | Hui et al. | |
| 5,521,202 A | 5/1996 | Yano et al. | |
| 5,709,874 A | 1/1998 | Hanson et al. | |
| 5,759,542 A | 6/1998 | Gurewich | |
| 5,840,674 A | 11/1998 | Yatvin et al. | |
| 5,860,957 A | 1/1999 | Jacobsen et al. | |
| 5,900,252 A | 5/1999 | Calanchi et al. | |
| 5,948,433 A | 9/1999 | Burton et al. | |
| 5,972,366 A | 10/1999 | Haynes et al. | |
| 5,983,134 A | 11/1999 | Ostrow | |
| 5,985,307 A | 11/1999 | Hanson et al. | |
| 5,985,317 A | 11/1999 | Venkateshwaran et al. | |
| 6,004,534 A | 12/1999 | Langer et al. | |
| 6,010,715 A | 1/2000 | Wick et al. | |
| 6,024,975 A | 2/2000 | D et al. | |
| 6,039,975 A | 3/2000 | Shah et al. | |
| 6,048,736 A | 4/2000 | Kosak | |
| 6,060,082 A | 5/2000 | Chen et al. | |
| 6,071,495 A | 6/2000 | Unger et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 7,763,747 B2 | 7/2010 | Snow et al. | |
| 8,143,424 B2 | 3/2012 | Chhipa et al. | |
| 8,168,775 B2 | 5/2012 | Sah et al. | |
| 8,226,977 B2 | 7/2012 | Kolatkar et al. | |

(Continued)

FOREIGN PATENT DOCUMENTS

DE 2834322 A1 2/1979
WO 1995012815 5/1995

(Continued)

OTHER PUBLICATIONS

International Search Report corresponding to PCT/US2018/000025 dated Jun. 15, 2018; 14 pages.
International Search Report and Written Opinion for PCT/US2019/023555, dated Jun. 6, 2019, 9 pages.
International Search Report and Written Opinion for PCT/US2019/046789, dated Oct. 21, 2019; 11 pages.
Partial Supplementary European Search Report corresponding to EP 18 75 3963 completed Oct. 29, 2020; 4 pages.
Extended European Search Report corresponding to EP 19770416.6 dated Nov. 10, 2021 (completed Oct. 27, 2021); 9 pages.

(Continued)

*Primary Examiner* — Gina C Justice
(74) *Attorney, Agent, or Firm* — Mintz Levin Cohn Ferris Glovsky and Popeo PC

(57) ABSTRACT

The present disclosure provides high-load tablet formulations of AG10 or a pharmaceutically acceptable salt thereof. In some aspects, provided herein are table formulations of AG10 or a pharmaceutically acceptable salt thereof that include at least 40% or more AG10 by weight and at least one pharmaceutical excipient selected from one or more fillers, one or more binders, one or more disintegrants, and one or more lubricants.

26 Claims, 9 Drawing Sheets

(56) References Cited

U.S. PATENT DOCUMENTS

| | | |
|---|---|---|
| 8,378,118 B2 | 2/2013 | Chhipa et al. |
| 8,552,034 B2 | 10/2013 | Verwijs et al. |
| 8,642,660 B2 | 2/2014 | Goldfarb |
| 8,877,795 B2 | 11/2014 | Graef et al. |
| 9,169,214 B2 | 10/2015 | Graef et al. |
| 9,308,209 B2 | 4/2016 | Graef et al. |
| 9,642,838 B2 | 5/2017 | Graef et al. |
| 9,913,826 B2 | 3/2018 | Graef et al. |
| 10,039,726 B2 | 8/2018 | Graef et al. |
| 10,278,929 B2 | 5/2019 | Graef et al. |
| 10,398,681 B2 | 9/2019 | Graef et al. |
| 10,513,497 B2 | 12/2019 | Chand et al. |
| 10,842,777 B2 | 3/2020 | Graef et al. |
| 11,058,668 B2 | 7/2021 | Sinha et al. |
| 11,078,162 B2 | 8/2021 | Chand et al. |
| 11,260,047 B2 | 3/2022 | Jernelius et al. |
| 2002/0048610 A1 | 4/2002 | Cima et al. |
| 2006/0160796 A1 | 7/2006 | Pfahl et al. |
| 2006/0183792 A1 | 8/2006 | Fobare et al. |
| 2007/0043096 A1 | 2/2007 | Tidmarsh et al. |
| 2008/0319077 A1 | 12/2008 | Suzuki et al. |
| 2009/0247547 A1 | 10/2009 | Shultz et al. |
| 2010/0183513 A1 | 7/2010 | Froestl et al. |
| 2010/0249094 A1 | 9/2010 | Yeung et al. |
| 2013/0095181 A1 | 4/2013 | Verwijs et al. |
| 2014/0179751 A1 | 6/2014 | Graef |
| 2017/0000807 A1 | 1/2017 | Koziara et al. |
| 2017/0029390 A1 | 2/2017 | Butler et al. |
| 2018/0125789 A1 | 5/2018 | Dalziel et al. |
| 2020/0016098 A1 | 1/2020 | Graef et al. |
| 2021/0260034 A1 | 8/2021 | Graef et al. |
| 2022/0016081 A1 | 1/2022 | Sinha et al. |
| 2022/0041558 A1 | 2/2022 | Chand et al. |
| 2023/0105307 A1 | 4/2023 | Graef et al. |

FOREIGN PATENT DOCUMENTS

| | | |
|---|---|---|
| WO | 2004096808 A1 | 11/2004 |
| WO | 2006009826 A1 | 1/2006 |
| WO | 2008077597 A1 | 7/2008 |
| WO | 2008141020 A1 | 11/2008 |
| WO | 2008145616 A1 | 12/2008 |
| WO | 2008154241 A1 | 12/2008 |
| WO | 2010010190 A1 | 1/2010 |
| WO | 2010030592 A1 | 3/2010 |
| WO | 2010059658 A1 | 5/2010 |
| WO | 2011046771 A1 | 4/2011 |
| WO | 2011053948 A1 | 5/2011 |
| WO | 2011140333 A1 | 11/2011 |
| WO | 2012082566 A1 | 6/2012 |
| WO | 2016025129 A1 | 2/2016 |
| WO | 2018/071678 A1 | 4/2019 |

OTHER PUBLICATIONS

Extended European Search Report corresponding to EP 19849948.5 dated Mar. 15, 2022 (completed Mar. 4, 2022); 6 pages.

Adamski-Werner, et al., Diflunisal Analogues Stabilize the Native State of Transthyretin. Potent Inhibition of Amyloidogenesis, J Med Chem , 2004 , pp. 355-374, vol. 47, No. 2.

Aldred , The cerebral expression of plasma protein genes in different species, Comp Biochem Physiol B Biochem Mol Biol., 1995, pp. 1-15, vol. 1, No. 1.

Alhamadsheh, et al., Potent Kinetic Stabilizers that Prevent Transthyretin-Mediated Cardiomyocyte Proteotoxicity, Sci. Transl. Med. , 2011, pp. 1-9, vol. 3, No. 97.

Arkin, et al., Small-molecule inhibitors of protein-protein interactions: progressing towards the dream, Nat Rev Drug Disco., 2004, pp. 301-317, vol. 3, No. 4.

Bartalena, et al., Thyroid hormone transport proteins, Clin Lab Med, 1993, pp. 583-598, vol. 13, No. 3.

Baures, STN International HCAPLUS database, (Columbus, Ohio), Accession No. 1998:617889, 1998.

Blake, et al., Structure of prealbumin: Secondary, tertiary and quaternary interactions determined by Fourier refinement at 1.8 A, J Mol Biol , 1978, pp. 339-356, vol. 121, No. 3.

Buxbaum, et al., Significance of the Amyloidogenic Transthyretin Val 122 ile allele in African Americans in the Arteriosclerosis Risk in Communities (ARIC) and Cardiovascular Health (CHS) Studies, Am Heart J, 2010, pp. 864-870, vol. 159.

Buxbaum, et al., Transthyretin protects Alzheimer's mice from the behavioral and biochemical effects of A. toxicity, Proc Natl Acad Sci., 2008, pp. 2681-2686, vol. 105, No. 7.

Caira, Mino R., "Crystalline Polymorphism of Organic Compounds," Topics in Current Chemistry (Jan. 1, 1998) 198:163-208.

Castano, Adam et al., "Natural history and therapy of TTR-cardiac amyloidosis: emerging disease-modifying therapies from organ transplantation to stabilizer and silencer drugs," Heart Fail Rev (2015; published online: Nov. 19, 2014) 20:163-178.

Chang, et al., Evolution of thyroid hormone binding by transthyretins in birds and mammals, Eur J Biochem., 1999, pp. 534-542, vol. 259.

Choi , et al. , "Accelerated AB Deposition in APPswe/PS1 delta E9 Mice with Hemizygous Deletions of TTR (Transthyretin)" , J Neurosci , 2007 , pp. 7006-7010, 27(26).

Choi, et al., Antidiabetic actions of a non-agonist PPARy ligand blocking Cdk5-mediated phosphorylation, Nature, 2011, pp. 477-481.

Coelho, Familial amyloid polyneuropathy: new developments in genetics and treatment, Current opinion in neurology, 1996, pp. 355-359, vol. 9, No. 5.

Connelly, et al., Structure-based design of kinetic stabilizers that ameliorate the transthyretin amyloidosis, Current Opinion in Structural Biology, 2010, pp. 54-62, vol. 20, No. 1.

Connors, et al., Cardiac amyloidosis in African Americans: Comparison of clinical and laboratory features of transthyretin V122I amyloidosis and immunoglobulin light chain amyloidosis, Am Heart J, 2009, pp. 607-614, vol. 158, No. 4.

Diana, et al., Synthesis and antiherpetic activity of some 4-[(aryloxy)alkyl]pyrazoles, Journal of Medicinal Chemistry, 1981, pp. 731-735, vol. 24, No. 6.

DiNunzio, James C. et al., "Use of highly compressible Celous™ microcrystalline cellulose for improved dosage form proeprties containing a hydrophilic solid dispersion," Drug Development and Industrial Pharmacy (2012; Published online Jul. 21, 2011) 38(2):180-189.

Emerson, et al., NMR characterization of interleukin-2 in complexes with the IL-2Ralpha receptor component, and with low molecular weight compounds that inhibit the IL-2/IL-Ralpha interaction, Protein Sci., 2003, pp. 811-822, vol. 12, No. 4.

Falk, et al., The Systemic Amyloidoses, N. Eng. J. Med., 1997, pp. 898-909, vol. 337.

Farr, et al., STN International HCAPLUS database, Accession No. 2001:338762, 2007.

Fujiwara, Mitsuko et al., "First-principles and direct design approaches for the control of pharmaceutical crystallization," Journal of Process Control (Aug. 1, 2005) 15(5):493-504.

Gell, et al. The Detection and Quantitation of Protein Oligomerization, Adv Exp Med Biol., 2012, pp. 19-41, vol. 747.

Haigis, et al., The Aging Stress Response, Mol Cell, 2010, pp. 333-344, vol. 40, No. 2.

He, et al., Small-molecule inhibition of TNF-alpha, Science, 2005, pp. 1022-1025, vol. 310, No. 5750.

Hull, et al., Islet amyloid: a critical entity in the pathogenesis of type 2 diabetes, J. Clin. Endocrinol & Metab, 2004, pp. 3629-3643, vol. 89, No. 8.

Jacobson, et al., Variant-Sequence Transthyretin (Isoleucine 122) in Late-Onset Cardiac Amyloidosis in Black Americans, N Engl J Med, 1997, pp. 466-473, vol. 336.

Jiang, et al., The V122I cardiomyopathy variant of transthyretin increases the velocity of rate-limiting tetramer dissociation, resulting in accelerated amyloidosis, Proc Natl Acad Sci USA, 2001, pp. 14943-14948, vol. 98, No. 26.

Joao, et al., Transthyretin mutations in health and disease, Hum Mutat, 1995, pp. 191-196, vol. 5.

(56) References Cited

OTHER PUBLICATIONS

Johnson, et al., Native State Kinetic Stabilization as a Strategy To Ameliorate Protein Misfolding Diseases: A on the Transthyretin Amyloidoses, Ace Chem Res, 2005, pp. 911-921, vol. 38, No. 12.
Katritzky, et al., Mannich reactions of carbonyl compounds and enamines with benzotriazole as the NH component, Journal of Heterocyclic Chemistry, 1994, pp. 917-923, vol. 31, No. 4.
Koehler, et al., Discovery of an inhibitor of a transcription factor using small molecule microarrays and diversity-oriented synthesis, J Am Chem Soc, 2003, pp. 8420-8421, vol. 125, No. 28.
Kucera, Sandra U. et al., "Evaluation of Ceolus™ microcrystalline cellulose grades for the direct compression of enteric-coated pellets," *Drug Development and Industrial Pharmacy* (2012; Published online Aug. 26, 2011) 38(3):341-350.
Maher, et al., Synthesis of some new 3-(2'-heterocyclicethyl)-2-methyl-3,4-dihydroquinazolin-4-one derivatives as antimicrobial agents, J Chem Tech & Biotech, 1992, pp. 209-215, vol. 55, No. 3.
Miller, et al., Enthalpy-Driven Stabilization of Transthyretin by AG10 Mimics a Naturally Occurring Genetic Variant That Protects from Transthyretin Amyloidosis, Journal of Medicinal Chemistry, Aug. 22, 2018, pp. 7862-7876, vol. 61, No. 17.
Miyawaki, Development of Probes for Cellular Functions Using Fluorescent Proteins and Fluorescence Resonance Energy Transfer, Annu Rev Biochem., 2011, pp. 357-373, vol. 7, No. 80.
Monaco, et al., Structure of a complex of two plasma proteins: transthyretin and retinol-binding protein, Science, 1995, pp. 1039-1047, vol. 268, No. 5231.
Morissette, Sherry L. et al., "High-throughput crystallization: polymorphs, salts, co-crystals and solvates of pharmaceutical solids," *Advanced Drug Delivery Reviews* (Feb. 23, 2004) 56(3):275-300.
National Center for Biotechnology Information. PubChem Compound Database; CID=71464713, https://pubchenn.ncbi.nlnn.nih.gov/ compound/71464713 (accessed Jan. 17, 2019).
Opadry AQ: Film coatings Opadry QX, Colorcon, 2016; pib_opadry QX_v1_04.2018; 6 pages.
Ouyang, et al., Syntheses of 4-(2-Hydroperoxy-2,2-diarylethyl)-3,5-dimethylpyrazoles, 4-(2-Hydroxy-2,2-diarylethyl)-3,5-dimethylpyrazoles, and the Related Compounds, Journal of Heterocyclic Chemistry, 1996, pp. 1291-1302, vol. 33, No. 4.
Penchala, et al., A Biomimetic Approach for Enhancing the in Vivo Half-Life of Peptides, Nature Chemical Biology, 2015, vol. 11, No. 10.
Penchala, et al., AG10 inhibits amyloidogenesis and cellular toxicity of the familial amyloid cardiomyopathy-associated V122I transthyretin, Proc Natl Acad Sci USA, Jun. 11, 2013, pp. 9992-9997, vol. 110, No. 24.
Peterson, et al., Inhibiting transthyretin conformational changes that lead to amyloid fibril formation, Proc Natl Acad Sci USA, 1998, pp. 12956-12960, vol. 95, No. 22.
Prapunpoj, et al., Change in structure of the N-terminal region of transthyretin produces change in affinity of transthyretin to T4 and T3, FEBS J, 2006, pp. 4013-4023, vol. 273, No. 17.
Ran, et al., Non-Conjugated Small Molecule FRET for Differentiating Monomers from Higher Molecular Weight Amyloid Beta Species, PLoS One, Apr. 2011, pp. 1-6, vol. 6, No. 4.
Reixach, et al., Tissue damage in the amyloidoses: Transthyretin monomers and nonnative oligomers are the major cytotoxic species in tissue culture, PNAS, Mar. 2, 2004, pp. 2817-2822.
Rickert, et al., The Structure of Interleukin-2 Complexed with its Alpha Receptor, Science, 2005, pp. 1477-1480, vol. 308, No. 5727.
Saraiva, et al., Transthyretin mutations in hyperthyroxinemia and amyloid diseases, Hum Mut., 2001, pp. 493-503, vol. 17, No. 6.
Sekijima, et al., Pathogenesis of and Therapeutic Strategies to Ameliorate the Transthyretin Amyloidoses, Curr Pharm Des, 2008, pp. 3219-3230, vol. 14, No. 30.
Selkoe, et al., Cell Biology of protein misfolding: The examples of Alzheimer's and Parkinson's diseases, Nat Cell Biol 6, 2004, pp. 1054-1061.
Selkoe, et al., Folding proteins in fatal ways, Nature, 2003, pp. 900-904, vol. 426.
Shukla, J.S. et al. "Studies on Neuropharmacological and Biochemical Properties of 5-Substituted Tetrazoles," Ind. J. Physiol. Pharmac. (Oct.-Dec. 1981), 25(4):369-373.
Stefani, Protein misfolding and aggregation: new examples in medicine and biology of the dark side of the protein world, Biochimica et biophysica acta, 2004, pp. 5-25, vol. 1739.
Suhr, et al., Liver Transplantation for Hereditary Transthyretin Amyloidosis, Transpl, 2000, pp. 263-276, vol. 6, No. 3.
Variankaval, Narayan et al., "From form to function: Crystallization of avctive pharmaceutical ingredients," *Aiche Journal* (published online Jun. 3, 2008) 54(7):1682-1688.
Wiseman, et al., Kinetic Stabilization of an Oligomeric Protein by a Single Ligand Binding Event, Am Chem Soc, 2005, pp. 5540-5551, vol. 127.
Wojtczak, et al., Structures of Human Transthyretin Complexed with Thyrixine at 2.0 A Resolution and 3', 5'-Dinitro-N-aceytyl-L-thyronine at 2,2 A Resolution, Acta Cryst., 1996, pp. 758-765, vol. D52.
Yamauchi, et al., STN International HCAPLUS database, (Columbus, Ohio), Accession No. 2003:155526.
Zefirov, et al., Ring-Opening Reactions of 1,1-diacetylcyclopropane with Hydrazine and Hydroxylamine Derivatives as the Novel Synthesis of p-X-ethyl Substituted Pyrazoles and Isoxazoles, Tetrahedron, 1982, pp. 1693-1697, vol. 38, No. 11.
Honda, Y et al., "2010 AAPS Annual Meeting and Exposition Poster. Direct compression of very high dose drug tablets using extremely compactible MCC, Ceolus™ KG-1000," Asahi Kasei Chemicals Corporation; 1 page.
2009 Post-Interphex Showcase: Chemicals, Raw Materials, Intemrediates, & Excipients, PharmTech.com; 3 pages.
Obae, Kasuiro, Ph.D., "Improving of compatibility and friability in high dose tablets living novel microcrystalline cellulose Ceolus™ KG-1000," *Asahi Kasei Chemical Corporation* (Apr. 16, 2008); 43 pages.
Serajuddin, Abu T.M., "Salt formation to improve drug solubility," *Advanced Drug Delivery Reviews* (May 29, 2007) 59:603-616.
Byrn, Stephen et al., "Pharmaceutical Solids: A Strategic Approach to Regulatory Considerations," *Pharmaceutical Research* (1995) 12(7):945-954.
Seppic: "Ceolus™ Microcrystalline Cellulose (MCC) used as compression excipients," retrieved from the internet at URL:<https://www.seppic.com/en/ceolus> (Jan. 27, 2017; retrieved on Aug. 27, 2023); 4 pages.
Kawaguchi, Yoko et al., "Drug and crystal polymorphism," *Seikatsu Kogaku Kenkyu*, vol. 4, No. 2, (2002), pp. 310-317.
Pharmaceuticals and Medical Devices Act, No. 568, 3.3.1. New drug substances, c) Polymorphic forms (May 1, 2001), 46 pages.
Oshima, Hiroshi; "Crystallization of Polymorphs and Pseudopolymorphs and Its Control," *Pharm Stage*, 2007, 6, 48-53.
Takada, Noriyuki; "API form screening and selection in drug discovery stage," *Pharm Stage*, 2007, 6, 20-25.
Yamano, Mitsuhisa, "Approach to Crystal Polymorph in Process Research of New Drug," *Journal of Synthetic Organic Chemistry*, 2007, 65, 907-913.

FORMULATIONS OF AG10

CROSS-REFERENCES TO RELATED APPLICATIONS

This application is a continuation application of U.S. patent application Ser. No. 16/542,737 filed Aug. 16, 2019, which application claims the benefit of priority under 35 U.S.C § 119(e) to U.S. Provisional Application Ser. No. 62/765,154 filed Aug. 17, 2018, the disclosure of each of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Aberrant protein interaction and aggregation, either through protein misfolding or over activation of a signaling pathway is the underlying cause of a large number of human degenerative diseases. As such, targeting protein interactions (PPIs) is of therapeutic interest.

To date approved inhibitors of PPIs are proteins rather than small-molecule inhibitors. For example, therapeutic monoclonal antibodies (mAbs) are used in treating cancer, autoimmune, infectious, and neuodegenerative diseases. Therapeutic mAbs are costly to manufacture, they require administration by injection, and can illicit an immune-response in the patient. For these reasons the development of small-molecule inhibitors of PPIs remains of interest.

One example of aberrant protein aggregation is the soluble protein transthyretin (TTR or prealbumin). Wild type (WT) TTR is a 55 kDa homotetrameric protein present in blood and cerebrospinal fluid. When dissociated from its homoterameric form, WT TTR dimers can misfold into amyloidogenic monomers. The formation of amyloidogenic monomers has been observed with WT TTR as well as more than 100 different mutated variants. Research has shown that stabilizing the tetrameric form of TTR inhibits the misfolding of amyloidogenic monomers and subsequent TTR amyloid formation.

Recent work has identified 3-(3-(3,5-dimethyl-1H-pyrazol-4-yl)propoxy)-4-fluorobenzoic acid (AG10) as a promising candidate to treat TTR amyloid related diseases such as TTR amyloid cardiomyopathy and ATTR polyneuropathy. This compound has been disclosed in WO 2014/100227. Despite the disclosure of this compound, improved pharmaceutical formulations that provide increased stability and consistent pharmacokinetic data remain elusive.

As such, there exists a need to produce pharmaceutical formulations suitable for administration to humans or other animals. The present disclosure addresses these needs and provides related advantages as well.

BRIEF SUMMARY OF THE INVENTION

The present disclosure provides high-load tablet formulations of AG10 or a pharmaceutically acceptable salt thereof and at least one pharmaceutical excipient selected from one or more fillers, one or more binders, one or more disintegrants, and one or more lubricants. In some embodiments, the tablet formulation is coated with a coating agent.

DETAILED DESCRIPTION OF THE INVENTION

I. General

Figure 1:
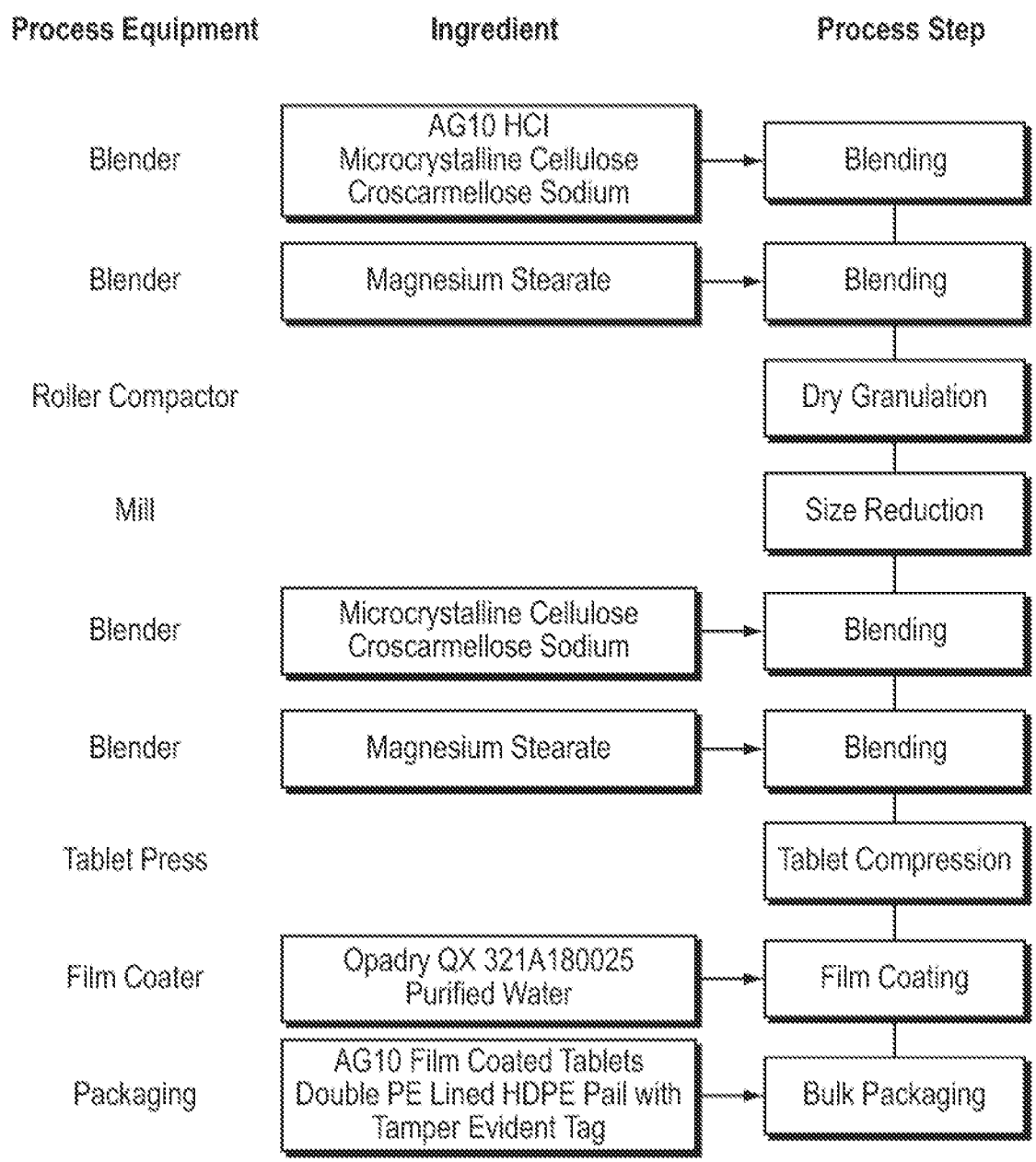
FIG. 1 illustrates the process flow diagram for preparing the AG10 formulations described in Example 2.

The present disclosure is based, in part, on the discovery that formulations containing 40% or more AG10 can be successfully prepared as tablets. These tablets are particularly well suited for administration to human and animal subjects alike because these amounts meet the necessary stability and pharmacokinetic requirements for oral formulations. Other formulations, such as capsules, fail to meet these needs.

High-load immediate release AG10 tablets were successfully achieved using a high grade microcrystalline cellulose. In contrast, tablet formulations exceeding 33.3% AG10 using standard grades of microcrystalline cellulose showed signs of tablet erosion after friability tests and reduced dissolution rates after extended storage times.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

The term "tablet" refers to solid pharmaceutical formulations with and without a coating. The term "tablet" also refers to tablets having one, two, three or even more layers, wherein each of the before mentioned types of tablets may be without or with one or more coatings. In some embodiments, tablets of the present disclosure can be prepared by roller compaction or other suitable means known in the art. The term "tablet" also comprises mini, melt, chewable, effervescent and orally disintegrating tablets. Tablets include AG10 and at least and one pharmaceutical excipient selected from one or more fillers, one or more binders, one or more disintegrants, and one or more lubricants. Optionally, a coating agent is also included. For the purposes of calculating percent weight of the tablet formulation, the amount of coating agent is not included in the calculation. That is, the percent weights reported herein are of the uncoated tablet.

The term "salt" refers to acid or base salts of the compounds of the present disclosure. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are nontoxic. Additional information on suitable pharmaceutically acceptable salts can be found in Remington's Pharmaceutical Sciences, 17th ed., Mack Publishing Company, Easton, Pa., 1985, which is incorporated herein by reference.

III. Embodiments of the Disclosure

The present disclosure provides, inter alia, tablet formulations of AG10 or a pharmaceutically acceptable salt thereof. AG10 is a compound having the formula:

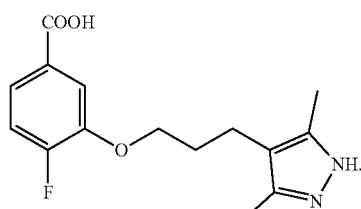

In some embodiments, a pharmaceutically acceptable salt of AG10 is corresponds to Formula I.

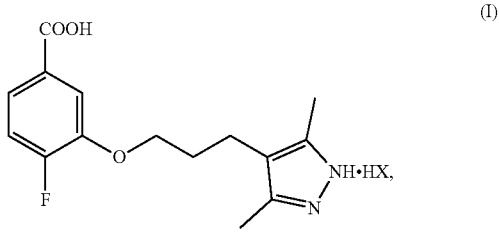

wherein X is a pharmaceutically acceptable anion of a protic acid.

A variety of protic acids are suitable for making a pharmaceutically acceptable salt of Formula I. It can be seen that the pharmaceutically acceptable anion of the protic acid is dependent upon the protic acid used. For example, protic acids useful in the present disclosure include hydrochloric acid, hydrobromic acid, sulfonic acid, tosylic acid (p-toluenesulfonic acid), methanesulfonic acid, nitric acid, or acetic acid. Thus, pharmaceutically acceptable anions of a protic acid include chloride ($Cl^-$), bromide (Br), sulfonate ($HS(O)_2O^-$), tosylate (TSO), mesylate ($MsO^-$), nitrate ($NO_3^-$) and acetate ($CH_3C(O)O^-$), or combinations thereof.

In some embodiments, the pharmaceutically acceptable anion of a protic acid is mesylate.

In some embodiments, the pharmaceutically acceptable anion of a protic acid is tosylate.

In some embodiments, the pharmaceutically acceptable anion of a protic acid is chloride, and the pharmaceutically acceptable salt of Formula I is represented by Formula (Ia)

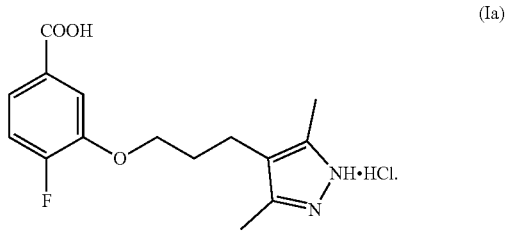

Pharmaceutically acceptable salts of Formula I can be produced using a number of conventional means in the art. For example, the free acid form of a compound of Formula I may be contacted with a stoichiometric amount of the appropriate acid in water, an organic solvent, or a mixture of the two. In some embodiments, pharmaceutically acceptable salts of Formula I are made in nonaqueous media such as an ether, ethyl acetate, ethanol, isopropanol, or acetonitrile. In some embodiments, the pharmaceutically acceptable salts of Formula I are made by dissolving a compound of Formula IX in water, adding a suitable amount of HX to form a mixture, and adding a nonaqueous solvent, such as the nonaqueous media described above to crystallize the salt. In some embodiments, a suitable amount of HX is a stoichiometric amount. It is understood the HX comprises a hydrogen and an X is a pharmaceutically acceptable anion of a protic acid as defined above.

The tablet formulations of the present disclosure can include, for example, about 40 to 85 or about 50 to 75% by weight of AG10 or a pharmaceutically acceptable salt thereof. In some embodiments, the tablet formulations contain about 50% to 70% by weight of AG10 or a pharmaceutically acceptable salt thereof. In some embodiments, the tablet formulations contain about 50% by weight of AG10 or a pharmaceutically acceptable salt thereof. In some embodiments, the tablet formulations contain about 66.7% by weight of AG10 or a pharmaceutically acceptable salt thereof. In some embodiments, the tablet formulations contain about 75% by weight of AG10 or a pharmaceutically acceptable salt thereof. In some embodiments, the tablet formulations contain about 80% by weight of AG10 or a pharmaceutically acceptable salt thereof. In some embodiments, the tablet formulations contain about 85% by weight of AG10 or a pharmaceutically acceptable salt thereof.

The amount of AG10 or a pharmaceutically acceptable salt thereof, in a tablet formulation can be about 0.1 to about 500 mg, about 0.1 to about 250 mg, or about 0.1 to about 100 mg. In some embodiments, the amount of AG10 present in a tablet formulation is about 10, 25, 50, 100, 200, 300, 400, or 500 mg. In some embodiments, the amount of AG10 present in a tablet formulation is about 50, 100, 200, or 400 mg. In some embodiments, the total weight (e.g., active ingredients plus excipients—not including coating) of the tablet formulation is about 50 to about 1500 mg. For example, the total weight of the solid dosage form is about 100, 150, 200, 300, 400, 500, 600, 700, 800, 900, 1000, or 1500 mg.

The tablet formulations of the present disclosure can include at least one ingredient selected from one or more fillers, one or more binders, one or more disintegrates, and one or more lubricants or other ingredient. In some embodiments, the tablet formulation comprises one or more excipients selected from a high grade microcrystalline filler, an inorganic salt filler, a disintegrant, and a lubricant.

In some embodiments, the tablet formulations of the present disclosure include one or more fillers. Suitable fillers are described below. In some embodiments, the one or more fillers are present in an amount of about 1 to 60, 5 to 55, 10 to 50, or 15 to 45% by weight. In some embodiments, one or more fillers are present in about 42.5% by weight. In some embodiments, one or more fillers are present in about 25.8% by weight. In some embodiments, one or more fillers are present in about 17.5% by weight.

In some embodiments, tablet formulations of the present disclosure include one to three fillers. In some embodiments, tablet formulations of the present disclosure include one to two fillers. In some embodiments, tablet formulations of the present disclosure include two fillers.

Suitable fillers include, for example, oligosaccharides (e.g., lactose), sugars, starches, modified starches, sugar alcohols (e.g. mannitol, sorbitol, xylitol, lactitol), inorganic salts, cellulose derivatives (e.g. microcrystalline cellulose, silicified microcrystalline cellulose, cellulose, hypromellose), calcium sulfate, aluminum and magnesium silicate complexes and oxides, and the like. Example of inorganic salt fillers include a phosphate salt, such as dibasic calcium phosphate dehydrate, salts of sulfates, and silicon dioxide. In some embodiments, the one or more fillers include cellulose derivatives or alkaline earth metal salts of chloride, phosphates, sulfates, and the like. In some embodiments, the one or more fillers include a cellulose derivative and an inorganic salt. In some embodiments, the one or more fillers are microcrystalline cellulose and silicon dioxide. In some embodiments, the one or more fillers are microcrystalline cellulose. In some embodiments, the microcrystalline cellulose is a high grade microcrystalline cellulose.

A high grade microcrystalline cellulose is a cellulose derived product that has specific properties that are not the dominant features in more standard preparations of microcrystalline cellulose. For example, in some embodiments, a high grade microcrystalline cellulose is characterized by cellulose polymers with spherical morphology and porous structure. These properties are found in UF grade microcrystalline cellulose from CEOLUS' (e.g. UF-702 and UF-711) and similar available products. In some embodiments, a high grade microcrystalline cellulose is characterized by cellulose polymers with needle-like particle shape. These properties are found in KG grade microcrystalline cellulose from CEOLUS' (e.g. KG-802 and KG-1000).

The high grade cellulose filler can be present in an amount of about 1 to 60% by weight. In some embodiments, the high grade microcrystalline cellulose is present in an amount of about 5 to 55% by weight. In some embodiments, the high grade microcrystalline cellulose is present in an amount of about 10 to 50% by weight. In some embodiments, the high grade microcrystalline cellulose is present in an amount of about 15 to 45% by weight. In some embodiments, the high grade microcrystalline cellulose is present in an amount of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45% by weight. In some embodiments, the high grade microcrystalline cellulose is present in an amount of about 17%. In some embodiments, the high grade microcrystalline cellulose is present in an amount of about 26%. In some embodiments, the high grade microcrystalline cellulose is present in an amount of about 42%.

In some embodiments, the tablet formulations of the present disclosure include one or more binders. Suitable binders are described below. In some embodiments, the one or more binders are present in an amount of about 0.5 to 15, about 0.5 to 10, or about 1 to 10% by weight. In some embodiments, the one or more binders are present in an amount of about 3 to 8% by weight. In some embodiments, the one or more binders are present in an amount of about 1, 2, 3, 4, 5, 6, 7, 8, 9, or 10% by weight. In some embodiments, the one or more binders are present in about 5% by weight.

In some embodiments, tablet formulations of the present disclosure include one to three binders. In some embodiments, tablet formulations of the present disclosure include one binder.

Suitable binders include, for example, povidone, lactose, starches, modified starches, sugars, gum acacia, gum tragacanth, guar gum, pectin, wax binders, methylcellulose, carboxymethylcellulose, hydroxypropyl methylcellulose, hydroxyethyl cellulose, hydroxypropyl cellulose, copolyvidone, gelatin, sodium alginate, and the like. Non-cellulosic binders include polymeric and other binders lacking a cellulose backbone. Examples of non-cellulosic binders include povidone, lactose, starches, modified starches, gums, guar gum, pectin, waxes, gelatins, alginates, and the like. In some embodiments, formulations contain a non-cellulosic binder such as povidone or copovidone. In some embodiments, the non-cellulosic binder is copovidone.

In some embodiments, the tablet formulations of the present disclosure include one or more disintegrants. Suitable disintegrants are described below. In some embodiments, the one or more disintegrants are present in an amount of about 1 to 15, about 1 to about 12, or about 1 to about 10% by weight. In some embodiments, one or more disintegrants are present in about 3-8% by weight. In some embodiments, the formulations contain about 3, 4, 5, 6, 7, or 8% by weight of disintegrant. In some embodiments, the formulations contain about 5% by weight of disintegrant. In some embodiments, the formulations contain about 6% by weight of disintegrant.

In some embodiments, tablet formulations of the present disclosure include one to three disintegrants. In some embodiments, tablet formulations of the present disclosure include one disintegrant.

Suitable disintegrants include, for example, croscarmellose sodium, crospovidone, polyvinylpyrrolidone, sodium starch glycolate, corn starch. In some embodiments, the formulations contain a disintegrant such as sodium starch glycolate or crospovidone. In some embodiments, the disintegrant is croscarmellose sodium.

In some embodiments, the tablet formulations of the present disclosure include one or more lubricants. Suitable lubricants are described below. In some embodiments, the one or more lubricants are present in an amount of about 0.1 to 8, 0.5 to 5, 0.5 to 3% by weight. In some embodiments, one or more lubricants are present in an amount of about 0.5, 0.75, 1, 1.5, 2, 3, 4, or 5% by weight. In some embodiments, one or more lubricants are present in an amount of about 2% by weight. In some embodiments, one or more lubricants are present in an amount of about 1.5% by weight.

In some embodiments, tablet formulations of the present disclosure include one to three lubricants. In some embodiments, tablet formulations of the present disclosure include one lubricant.

Suitable lubricants include, for example, magnesium stearate, stearic acid, palmitic acid, calcium stearate, talc, carnauba wax, hydrogenated vegetable oils, mineral oil, polyethylene glycols, and sodium stearyl fumarate. In some embodiments, the one or more lubricants are magnesium stearate and/or sodium stearyl fumarate. In some embodiments, the one or more lubricants is magnesium stearate.

Other suitable fillers, binders, disintegrants, lubricants and other excipients which may be used are described in Handbook of Pharmaceutical Excipients, 2nd Edition, American Lachman, Leon, 1976; Pharmaceutical Dosage Forms: Tablets Volume 1, 2nd Edition, Lieberman, Herbert A., et al, 1989; Modern Pharmaceutics, Banker, Gilbert and Rhodes, Christopher T, 1979; and Remington's Pharmaceutical Sciences, 15th Edition, 1975, each of which is incorporated herein by reference in its entirety.

In some embodiments, the tablet is coated with a coating agent. Suitable coating agents include ethylcellulose, polymethacrylates, as well as coating products sold by OPADRY™. In some embodiments, the coating agent is Opadry Clear, Opadry Blue 13B50579, Opadry White 33628707, Opadrya QX 321A180025, or Opadry II (33G28707). In some embodiments the coating agent is Opadry White 33628707. In some embodiments the coating agent is Opadry QX 321A180025. In some embodiments the coating agent is Opadry II (33G28707). For the purposes of calculating percent weight of the tablet formulation, the amount of coating agent is not included in the calculation. That is, the percent weights reported herein are of the uncoated tablet.

In some embodiments, the tablet formulation contains about 40 to 85% by weight of AG10 or a pharmaceutically acceptable salt thereof; about 5 to 55% by weight of one or more fillers; about 0 to 15% by weight of one or more binders; about 1 to 15% by weight of one or more disintegrants; and about 0.1 to 8% by weight of one or more lubricants. In some embodiments, the noted formulation includes a coating agent.

In some embodiments, the tablet formulation contains about 50 to 75% by weight of AG10 or a pharmaceutically acceptable salt thereof; about 10 to 50% by weight of one or more fillers; about 3 to 8% by weight of one or more disintegrants; and 0.5 to 3% by weight of one or more lubricants. In some embodiments, the noted formulation includes a coating agent.

In some embodiments, the tablet formulation contains about 50% by weight of AG10 or a pharmaceutically acceptable salt thereof; about 42.5% by weight of one or more fillers; about 6% by weight of a disintegrant; and about 1.5% by weight of a lubricant. In some embodiments, the noted formulation includes a coating agent.

In some embodiments, the tablet formulation contains about 66.7% by weight of AG10 or a pharmaceutically acceptable salt thereof; about 25.8% by weight of one or more fillers; about 6% by weight of a disintegrant; and about 1.5% by weight of a lubricant. In some embodiments, the noted formulation includes a coating agent.

In some embodiments, the tablet formulation contains about 75% by weight of AG10 or a pharmaceutically acceptable salt thereof; about 17.5% by weight of one or more fillers; about 6% by weight of a disintegrant; and about 1.5% by weight of a lubricant. In some embodiments, the noted formulation includes a coating agent.

In some embodiments, the tablet formulation of the present disclosure are at least 75% dissolved after 10 minutes in a solution of 0.1N HCl at 37±0.5° C. in an Apparatus-II (Paddles) with a paddle speed of about 50 rpm. In some embodiments, the tablet formulation of the present disclosure are at least 85% dissolved after 10 minutes in a solution of 0.1N HCl at 37±0.5° C. in an Apparatus-II (Paddles) with a paddle speed of about 50 rpm. In some embodiments, the tablet formulation of the present disclosure are at least 95% dissolved after 10 minutes in a solution of 0.1N HCl at 37±0.5° C. in an Apparatus-II (Paddles) with a paddle speed of about 50 rpm. In some embodiments, the tablet is tested was prepared within a week of the dissolution test. In some embodiments, the tablet is tested was prepared at least a month before performing the dissolution test. In some embodiments, the tablet is tested was prepared at least a three months before performing the dissolution test. In some embodiments, the tablet is tested was prepared at least six months before performing the dissolution test. In some embodiments, the tablet was incubated for one month at 25° C. with 60% relative humidity (RH) before performing the dissolution test. In some embodiments, the tablet was incubated for two months at 25° C. with 60% relative humidity (RH) before performing the dissolution test. In some embodiments, the tablet was incubated for three months at 25° C. with 60% relative humidity (RH) before performing the dissolution test. In some embodiments, the tablet was incubated for one month at 40° C. with 75% relative humidity (RH) before performing the dissolution test. In some embodiments, the tablet was incubated for three months at 40° C. with 75% relative humidity (RH) before performing the dissolution test. In some embodiments, the tablet was incubated for six months at 40° C. with 75% relative humidity (RH) before performing the dissolution test.

IV. Examples

The following examples are offered to illustrate, but not to limit, the claimed invention.

Example 1: Capsule & Tablet Evaluation, Capsules Provide Inconsistent Oral Pharmacokinetic Data Pharmacokinetics of AG10 were determined when administered once daily to dogs via oral gavage at 20, 60, and 200 mg/kg for 3 days (Study No. 1). Each group consisted of two animals/sex/group. Blood samples were collected from each animal on Day 1 at pre-dose, 0.25, 0.5, 1, 2, 4, 8, 12 and 24 hours post-dose, Day 3 at pre-dose, 0.25, 0.5, 1, 2, 4, 8, 12, 24, 48 and 72 hr post-dose. Plasma samples were assayed for AG10 by LC-MS/MS. In general, no sex differences in AG10 mean $C_{max}$ and $AUC_{0-24}$ values were observed; therefore, results for the 20 mg/kg dose group are presented as combined sex values in Table 1 below.

The pharmacokinetics of AG10 were also determined following oral administration in non-naïve male and female beagle dogs (Study No. 2). The study design included three treatment groups (n=2/sex/group). Groups 1 and 2 received 5 mg/kg and 20 mg/kg AG10 in 0.5% methylcellulose (MC) formulations respectively. Group 3 animals received 20 mg/kg AG10 in gelatin capsule form. Blood samples were collected at pre-dose and approximately 2, 4, 6, 8, 12, and 24 hours post-dose. Plasma samples were assayed for AG10 by LC-MS/MS. Plasma exposures ($AUC_{0-24}$) of AG10 in dogs administered 20 mg/kg AG10 as a suspension in 0.5% methylcellulose were similar to those obtained in Study No. 1 (Table 1). Plasma exposures of AG10 were also similar in dogs which were administered the same dose of AG10 either as a suspension in 0.5% methylcellulose or as a gelatin capsule without any excipients.

AG10 was administered orally to 4 male beagle dogs each as a 50 mg tablet, 200 mg tablet, and a 200 mg capsule (No. 3). Blood samples were collected at pre-dose and approximately 0.25, 0.5, 1, 2, 4, 8, 24, 48, 72 and 96 hours post-dose. Plasma samples were assayed for AG10 by LC-MS/MS. The $C_{max}$ and $AUC_{0-inf}$ values for dogs dosed with 200 mg tablets and 200 mg capsules were not significantly different (P<0.05) as determined by an unpaired t-test (P values of 0.0788 and 0.0995 for $C_{max}$ and $AUC_{0-inf}$ respectively).

TABLE 1

Comparison of the Pharmacokinetics of Various Formulations of AG10 Administered by Oral Gavage to Dogs

| Study | Formulation | Dose | Sex | $C_{max}$ (µg/mL) | $AUC_{0-24}$ (µg*hr/mL) |
|---|---|---|---|---|---|
| No. 1 | 0.5% MC | 20 mg/kg | MF | 16.1 | 69.1 |
| No. 2 | 0.5% MC | 20 mg/kg | MF | 8.10 | 71.2 |
|  | Capsule | 20 mg/kg | MF | 10.3 | 89.3 |
| No. 3 | Tablet | 50 mg | M | 4.66 | 41.5 |
|  | Tablet | 200 mg | M | 13.0 | 88.0 |
|  | Capsule | 200 mg | M | 9.33 | 65.7 |

In dog studies comparing methylcellulose formulations of AG10, time to maximal concentration (Tmax) was 0.44±0.38 hr in study No. 1 and 2.5±1 hr in study No. 2. The capsule in study No. 2 was formulated without excipients and showed lower variability (Tmax=2±0 hr) than the methylcellulose comparator. In study No. 3, even though the maximal exposure of AG10 tablets was comparable to that of the capsule, animal to animal variability in absorption of AG10 was greater in the four animals orally dosed with capsule containing excipients. For the 50 mg tablets, time to maximal concentration (Tmax) was 0.500±0 hr, for the 200 mg tablets, Tmax was at 1.00±0 hr. For 200 mg capsules with excipient, Tmax was more variable at 1.38±0.750 hr. Thus, in the head to head comparison, tablets produced more consistent oral ab sorption of AG10.

Example 2: High-Load Immediate Release Tablet Formulations of AG10

The following Example describes the successful preparation of tablet formulations containing high amounts of AG10.

Three tablet formulations containing differing amounts of AG10 were prepared. Table 2 provides information on the relative amounts of components used in each formulation.

TABLE 2

High-Load AG10 Tablet Formulations

| Ingredient | Grade | Batch 1 | Batch 2 | Batch 3 |
|---|---|---|---|---|
| INTRAGRANULAR ||||| 
| AG10 (HCl salt) |  | 50.00 | 66.67 | 75.00 |
| Microcrystalline Cellulose | Ceolus UF711 | 32.25 | 20.58 | 12.25 |
| Croscarmellose Sodium | SDW-802 | 3.00 | 3.00 | 3.00 |
| Silicon Dioxide | Syloid 244 | 0.25 | 0.25 | 0.25 |
| Magnesium Stearate | Ligamed MF-2-K | 0.75 | 0.75 | 0.75 |
| EXTRAGRANULAR ||||| 
| Microcrystalline Cellulose | Ceolus UF711 | 10.00 | 5.00 | 5.00 |
| Croscarmellose Sodium | SDW-802 or Ac-Di-Sol SD-711 | 3.00 | 3.00 | 3.00 |
| Magnesium Stearate | Ligamed MF-2-K | 0.75 | 0.75 | 0.75 |
| Total |  | 100.00 | 100.00 | 100.00 |

After compression, the tablets were film coated with OpadryQX white.

Tablets were prepared using the general diagram provided in FIG. 1. Table 3 below, provides an exemplary amounts used in formulating a tablet formulation with 66.7% AG10 HCl (Batch 2), and Table 4 and Table 5 provide a list of equipment used and a summary of the steps performed to prepare the tablet formulation. Similar processes were performed when preparing Batch 1 and Batch 3, referenced in Table 2.

TABLE 3

High-Load AG10 Tablet Formulations

| Item No. | Ingredient | Grade | Batch 2 |
|---|---|---|---|
| INTRAGRANULAR |||| 
| 1 | AG10 (HCl salt) |  | 937.62 g |
| 2 | Microcrystalline Cellulose | Ceolus UF711 | 219.11 |
| 3 | Croscarmellose Sodium | SDW-802 | 42.19 |
| 4 | Silicon Dioxide | Syloid 244 | 3.52 |
| 5 | Magnesium Stearate | Ligamed MF-2-K | 10.55 |
| EXTRAGRANULAR |||| 
| 6 | Microcrystalline Cellulose | Ceolus UF711 | 133.13 |
| 7 | Croscarmellose Sodium | SDW-802 or Ac-Di-Sol SD-711 | 39.94 |
| 8 | Magnesium Stearate | Ligamed MF-2-K | 9.99 |

TABLE 4

Equipment Used
Items Used

| | |
|---|---|
| Maxiblender | Sterile singe use scoop |
| 16 qt tote | Bosch press, TPR 200 |
| Sample thief | Caliper |
| #20 ss Mesh sieve | Tablet Hardness tester |
| #30 ss Mesh sieve | Solidlab 1 coater |
| Sieve Pan | 13' coating pan |

TABLE 5

Summary of Procedure

Transfer item No. 1, 2, and 3 into 16-quart tote
Blend for 5 minutes at 25 rpm
Take small portion of blend in previous step and mix with item No. 4, sieve blend through a #30 mesh sieve, transfer blend with item No. 4 into the 16-quart tote
Blend for 5 minutes at 25 rpm
Transfer item No. 5 into the 16-quart tote
Blend for 3 minutes at 25 rpm Transfer blend into the roller compactor with the following settings

| | |
|---|---|
| Gap Width | 2.0 (1.0-3.0) mm |
| Compaction Force | 8.0 (2-10) kN/cm |
| Granulator Speed Clockwise | 65 (25-125) rpm |
| Granulator Speed Counter Clockwise | 65 (25-125) rpm |
| Granulator Angle Clockwise | 360° |
| Granulator Angle Counter Clockwise | 330° |
| Tampt to feed auger ration | 185 (100-300) % |
| Agitatory Speed | 6 (1-20) rpm |
| Gap between granulator screen and granulator | 1.25 mm |
| Gap control | On |
| Torque control | Off |
| Feed factor | 0.60 (0.30-0.80) |
| PID | 2/12,000/0 |

Adjust amounts of extragranular components (item No. 6, 7, and 8) based on yield of milled granules
Transfer milled granules to 16 quart tote, add item No. 6 and 7, and blend for 5 minutes at 25 rpm
Add item No. 8 to 16-quarte tote and blend for 3 minutes at 25 rpm Compress the blend in a Bosch Press using the following parameters

| | |
|---|---|
| Feeder Speed | 8-10 |
| Press Speed | 20 RPM |
| Pre-Compression Force | 1.3-1.5 kN |
| Compression Force | 19.5-21.7 kN |

Coat tablets with Opadry QX 321A180025 using known methods in the art

Figure 2:
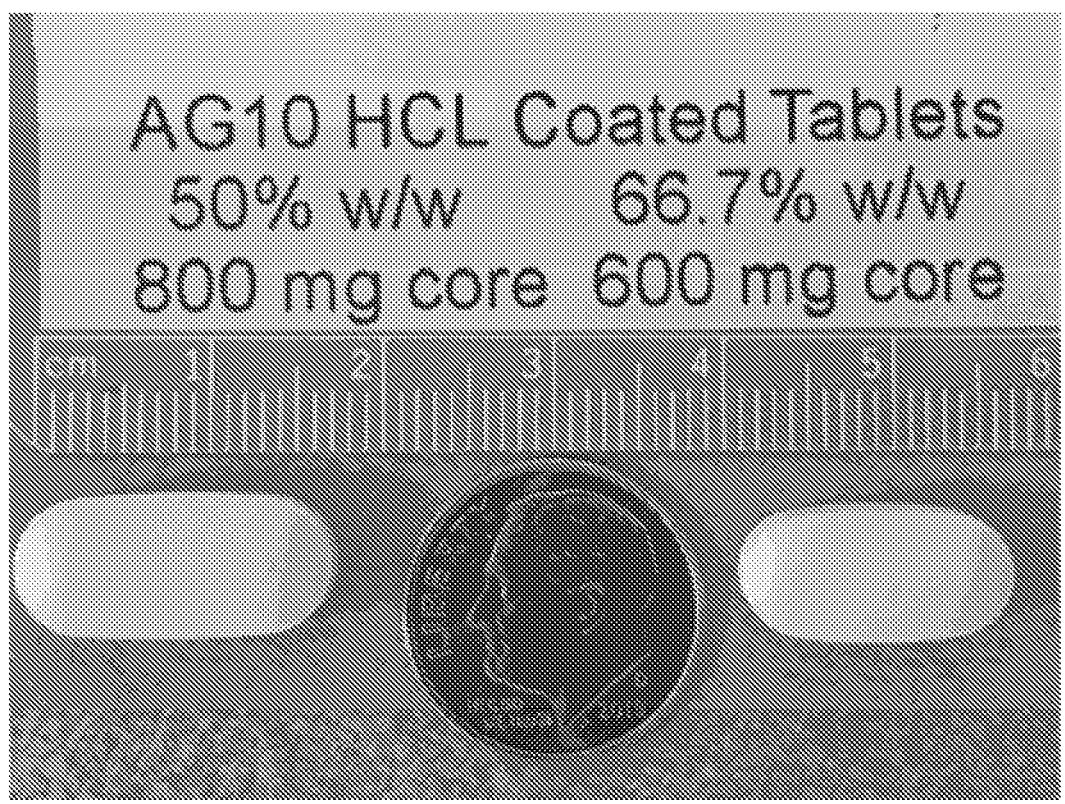
FIG. 2 shows images of the AG10 HCl coated tablets prepared in Example 2.

A picture of a 50% (w/w) and a 66.7 (w/w) AG10 HCl coated tablets are shown in FIG. 2 The 50% tablet was compressed with 8×17.5 mm capsule shaped tooling, while 66.7% tablet was compressed at 7.5×15 mm capsule tooling. Physical properties of the two displayed tablets are summarized in Table 6.

TABLE 6

Summary of Physical Properties

| Formulation Description | Average Thickness (mm) | Average Hardness (kP) | Disintegration Time (mm:ss) | Bulk Density (g/mL) | Tapped Density (g/mL) | Friability (%) |
|---|---|---|---|---|---|---|
| 50% w/w HCl salt | 6.18 | 21.7 | 1:00 | 0.53 | 0.70 | 0.0 |
| 66.7% w/w HCl salt | 5.96 | 16.6 | 0:45 | 0.57 | 0.69 | 0.0 |

Measurement of friability: Friability of the tablets, as reported in Table 6, was evaluated according to USP method <1216> from the percentage weight loss of NLT 6.5 g of tablets tumbled in a friabilator (model EF-2, Electrolab) for 100 rounds at 25 rpm. The tablets were dedusted, and the loss in weight caused by fracture or abrasion was recorded as the percentage weight loss. Friability below 1% is considered acceptable.

Next, dissolution profiles of a 50% (w/w) and a 66.7 (w/w) AG10 HCl coated tablets were determined. The dissolution experiments were performed by placing a tablet formulation in a solution of 0.1N HCl described in Table 7.

TABLE 7

Dissolution Parameters

| | |
|---|---|
| Medium: | 900 mL of 0.1N HCl |
| Temperature: | 37.0 ± 0.5° C. |
| Apparatus: | II (Paddles) |
| Speed: | 50 rpm, ramp to 200 rpm after 45 minutes |
| Sampling times: | 10, 20, 30, 45, and 60 minutes |
| Sampling volume: | 1 ml |
| Filter: | 0.45 μm GHP filter |

Figure 3:
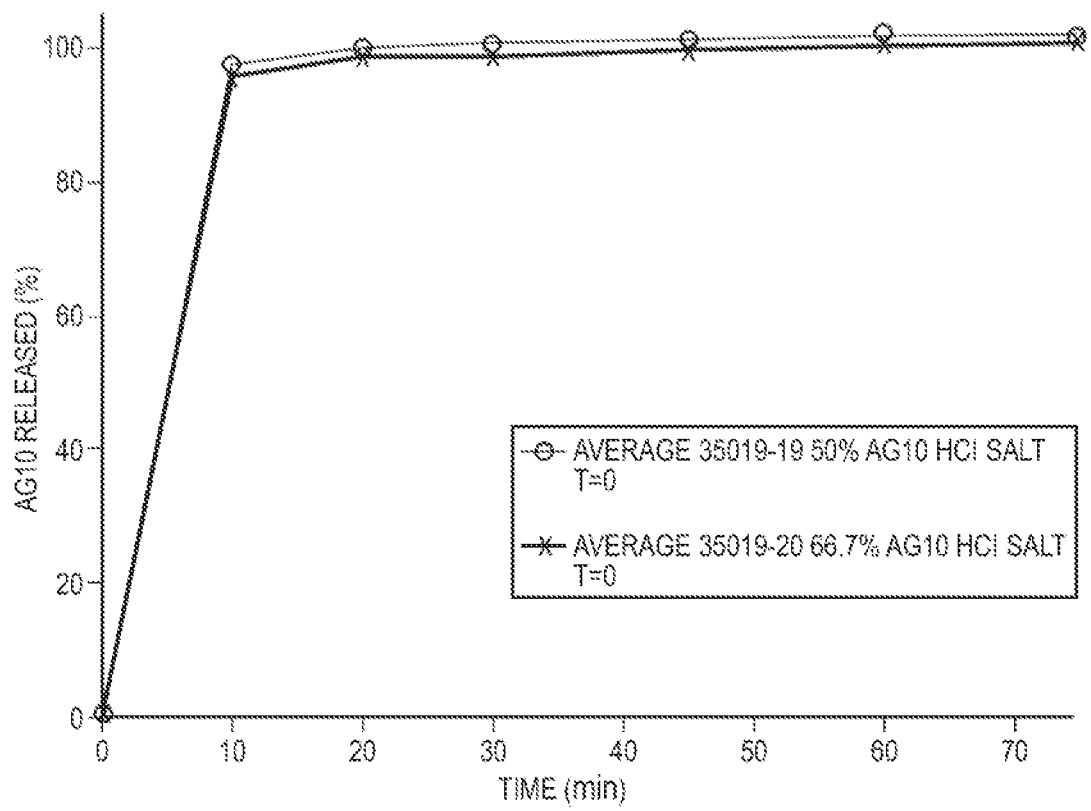
FIG. 3 show the dissolution profile for AG10 solid tablets formulations described in Example 2.

FIG. 3 shows the dissolution profiles of a 50% (w/w) and a 66.7 (w/w) AG10 HCl coated tablets. The dissolution experiment was performed with no significant incubation time after the tablet was formulated. As seen in FIG. 3 dissolution reached 100% released within 10 minutes for both tablets.

Example 3: Tablet Formulations Exceeding 33.3% AG10 Exhibited Tablet Erosion During Friability Test The following example describes tablet formulations of AG10 where 33.3% drug loading could not be exceeded without experiencing tablet erosion during friability test.

Figure 4:
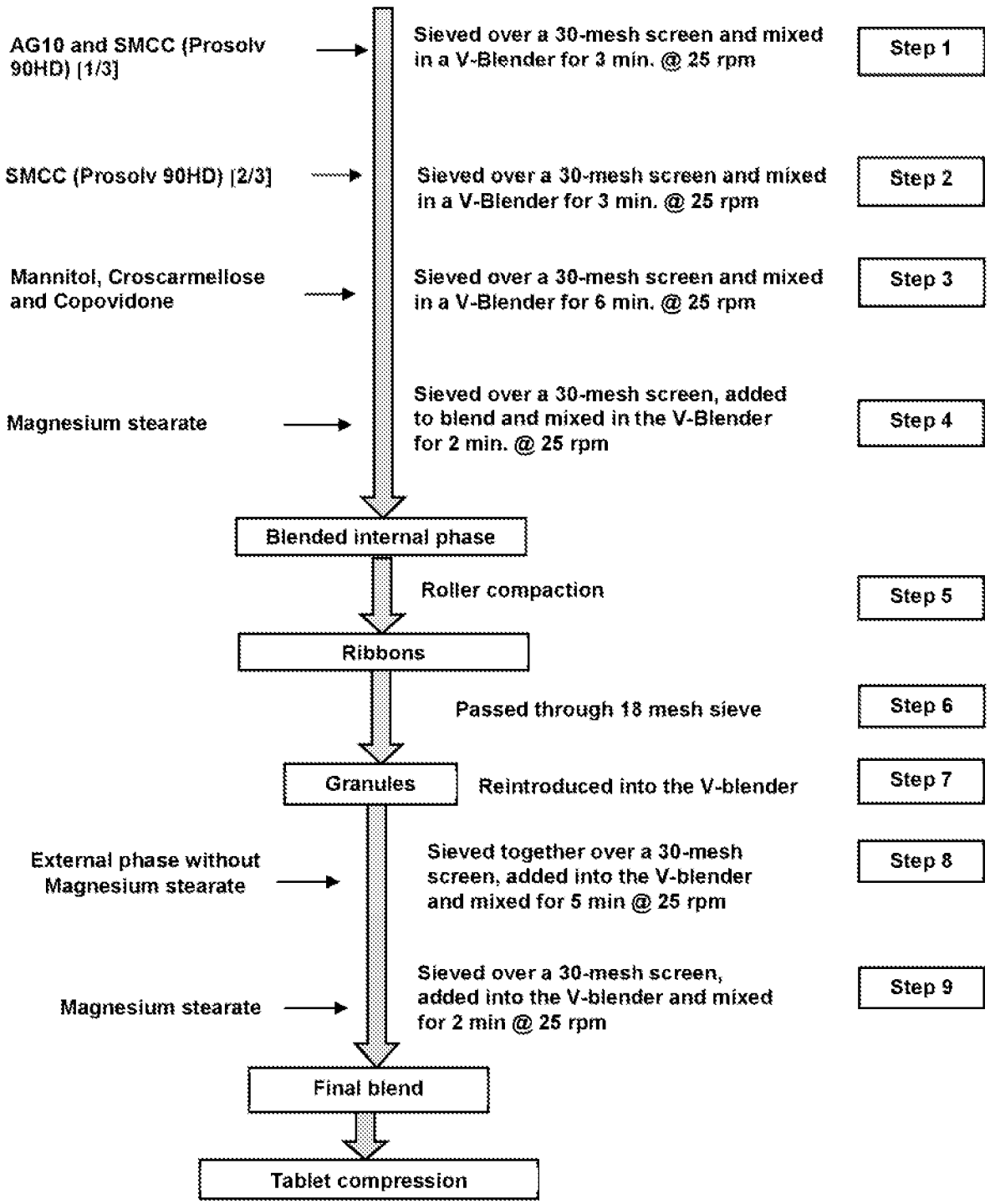
FIG. 4 illustrates the process flow diagram for preparing the AG10 formulations described in Example 3.
Figure 5:
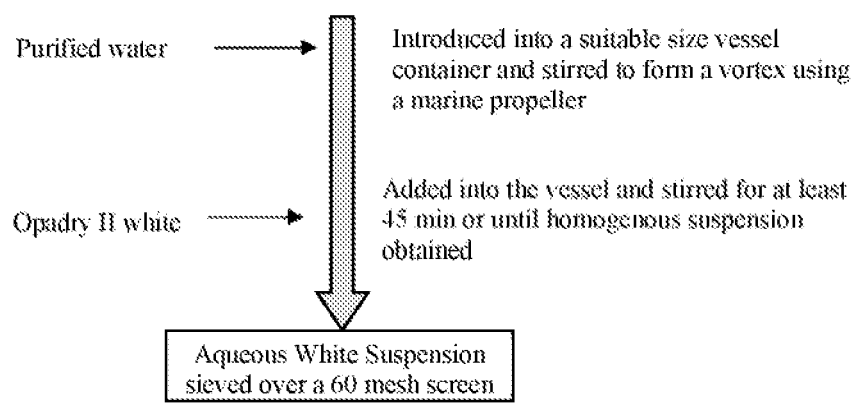
FIG. 5 illustrates the process flow for aqueous coating suspension preparation or preparing the AG10 formulations described in Example 3.

Formulations of AG10 were prepared as generally outlined in FIG. 4 and FIG. 5. The amount of AG10 and other components are area described in Table 8.

TABLE 8

AG10 Tablet Formulations Prepared

| Ingredient | Grade | L016 | L017 | L018A/B |
|---|---|---|---|---|
| INTRAGRANULAR | | | | |
| AG10 (HCl salt) | | 40.0 | 40.0 | 33.00 |
| Silicified Microcrystalline Cellulose | Prosolv HD90 | 24.0 | 26.0 | — |
| Mannitol | Type 100 SD | 16.0 | 20.0 | 28.0 |
| Copovidone | S-630 | 5.0 | 5.0 | 20.0 |
| Croscarmellose sodium | Type A | 3.0 | 3.0 | 5.0 |
| Magnesium Stearate | Ligamed MF-V2 | 1.3 | 1.0 | 3.0 |
| EXTRAGRANULAR | | | 2.0 | 1.0 |
| Mannitol | Type 100 SD | 8.0 | 2.0 | 7.0 |
| Croscarmellose Sodium | Type A | 2.0 | 1.0 | 2.0 |
| Magnesium Stearate | Ligamed MF-V2 | 0.7 | 40.0 | 1.0 |
| Total | | 100.0 | 100.0 | 100.0 |

Figure 6:
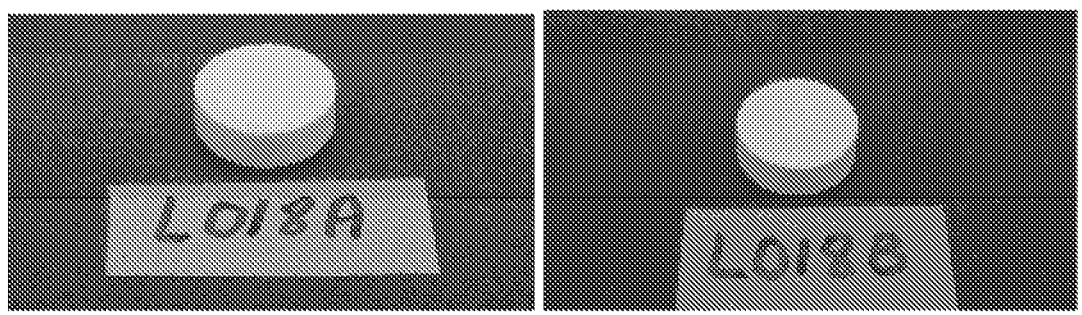
FIG. 6 shows images illustrating the lack of tablet edge's erosion after friability test for L018A (High hardness, Left), and L018B (Middle hardness, Right) (at 33.0% AG10).
Figure 7:
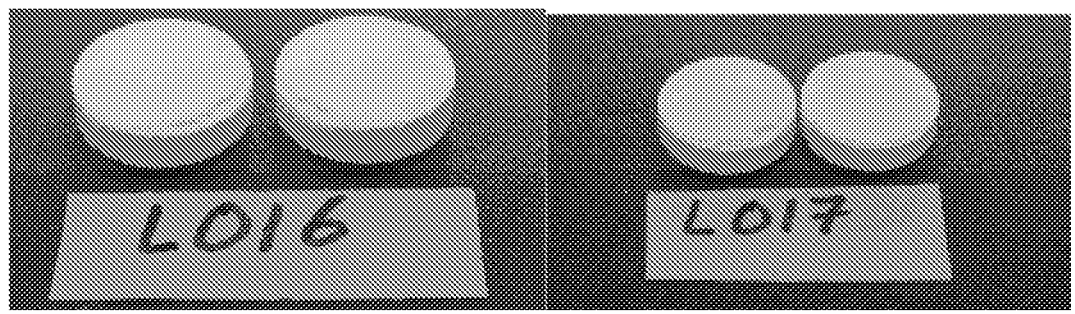
FIG. 7 shows images of major tablet edge's erosion after friability test for L016 (Left), and for L017 (Right) (Both formulations have a 40% AG10 load and maximum hardness).

Each of the above referenced formulations were prepared as 200 mg tablets and underwent a friability test as described in Example 2. Tablets from L018A and L018B prepared at 33.0% drug load (and compressed at high and middle hardness kP values, respectively) were resistant to crumbling, presenting only minor (if any) tablet edge erosion after friability test. See, FIG. 6. Comparatively, L016 and L017, prepared at 40% drug load and compressed at the maximum hardness that could be reached, presented major tablet edge erosion after friability test. See, FIG. 7.

The formulations discussed above used a standard grade of microcrystalline cellulose, and the resulting tablets with greater than 33.0% AG10 had friability issues that compromise their clinical use. Comparatively, the formulations of Example 2 used high grade microcrystalline cellulose, and reliably provided tablets that had favorable physical properties and were not susceptible to crumbling.

Example 4: "Accelerated Stability Condition" Dissolution Test Demonstrates High-Load AG10 Tablet Formulation Stability The following Example describes the preparation and subsequent dissolution tests of immediate release tablet formulations containing 33% AG10 HCl (200 mg) with standard microcrystalline cellulose and tablet formulations containing 66.7% AG10 HCl (400 mg) with a high grade microcrystalline cellulose.

The formulations for each of the tablets are shown in Table 9 and Table 10, respectively.

TABLE 9

Quantitative Composition of 33% AG10 HCl Tablets

| Ingredient | Quantitative Composition (% w/w) | Quantity per Tablet (mg) | Quality Standard |
|---|---|---|---|
| AG10 Hydrochloride[a] | 33.00 | 200.0 | In-house |
| Silicified Microcrystalline Cellulose[a,b] | 28.00 | 169.7 | NF |
| Mannitol[c] | 20.00 | 121.2 | USP |
| Croscarmellose Sodium[d] | 3.00 | 18.2 | NF |
| Copovidone[e] | 5.00 | 30.3 | NF |
| Magnesium Stearate[f] | 1.01 | 6.1 | NF |
| Mannitol[c] | 10.00 | 60.0 | USP |
| Croscarmellose Sodium[d] | 3.00 | 180 | NF |
| Magnesium Stearate[f] | 0.75 | 4.5 | NF |
| Total: | 100.0 | 606.0 | — |
| Purified Water[g] | N/A | N/A | USP |
| Opadry White 33G28707[h] | 3% | 18.2 mg | In-house |

[a]Actual amount of AG10 hydrochloride is adjusted based on drug substance potency and corresponds to 177.82 mg of AG10 free base. The actual amount of silicified microcrystalline cellulose is based on a concomitant reduction such that the target core weight remains 606 mg.
[b]Prosolv HD 90
[c]Pearlitol 100SD
[d]Solutab type A
[e]Plasdone S-630
[f]Ligamed MF-2-V
[g]Purified water is used in the film coating process and is removed during processing
[h]Represents 3% weight gain on the tablet core weight. Opadry White, Colorcon 33G28707 contains Hypromellose (Ph. Eur.), titanium dioxide (Ph. Eur.), and triacetin (Ph. Eur.).

TABLE 10

Quantitative Composition of 66.7% AG10 HCl Tablets

| Ingredient | Quantitative Composition (% w/w) | Quantity per Tablet (mg) | Quality Standard |
|---|---|---|---|
| Intragranular | | | |
| AG10 Hydrochloride[a] | 66.67 | 400.0 | In-house |
| High Grade Microcrystalline Cellulose[a,b] | 15.58 | 93.5 | NF/Ph. Eur. |
| Croscarmellose Sodium[c] | 3.00 | 180 | NF/Ph. Eur. |
| Silicon Dioxide, Colloidal[d] | 0.25 | 1.5 | NF/Ph. Eur. |
| Magnesium Stearate[e] | 0.75 | 4.5 | NF/Ph. Eur. |
| Extragranular | | | |
| Microcrystalline Cellulose[b] | 10.00 | 60.0 | NF/Ph. Eur. |
| Croscarmellose Sodium[c] | 3.00 | 180 | NF/Ph. Eur. |
| Magnesium Stearate[e] | 0.75 | 4.5 | NF/Ph. Eur. |
| Total: | 100.0 | 600.0 | — |
| Film Coat | | | |
| Purified Water[f] | N/A | N/A | USP/Ph. Eur |
| Opadry QX White[g] | 4% | 24 mg | In-house |

[a]Actual amount of AG10 hydrochloride is adjusted based on drug substance potency and corresponds to 355.64 mg of AG10 free base. The actual amount of microcrystalline cellulose is based on a concomitant reduction such that the target core weight remains 600 mg
[b]Ceolus UF-711 or equivalent
[c]Ac-Di-Sol SD711 or equivalent
[d]Syloid 244 FP or equivalent
[e]Hyqual 5712, Ligamed MF-2-K, or equivalent
[f]Purified water is used in the film coating process and is removed during processing
[g]Represents 4% weight gain on the tablet core weight. Opadry QX White, Colorcon 321A180025 contains GMCC type 1/mono- and di-glycerides, polyethylene glycol polyvinyl alcohol graft copolymer, polyvinyl alcohol (partially hydrolyzed), talc, and titanium dioxide.

Figure 8:
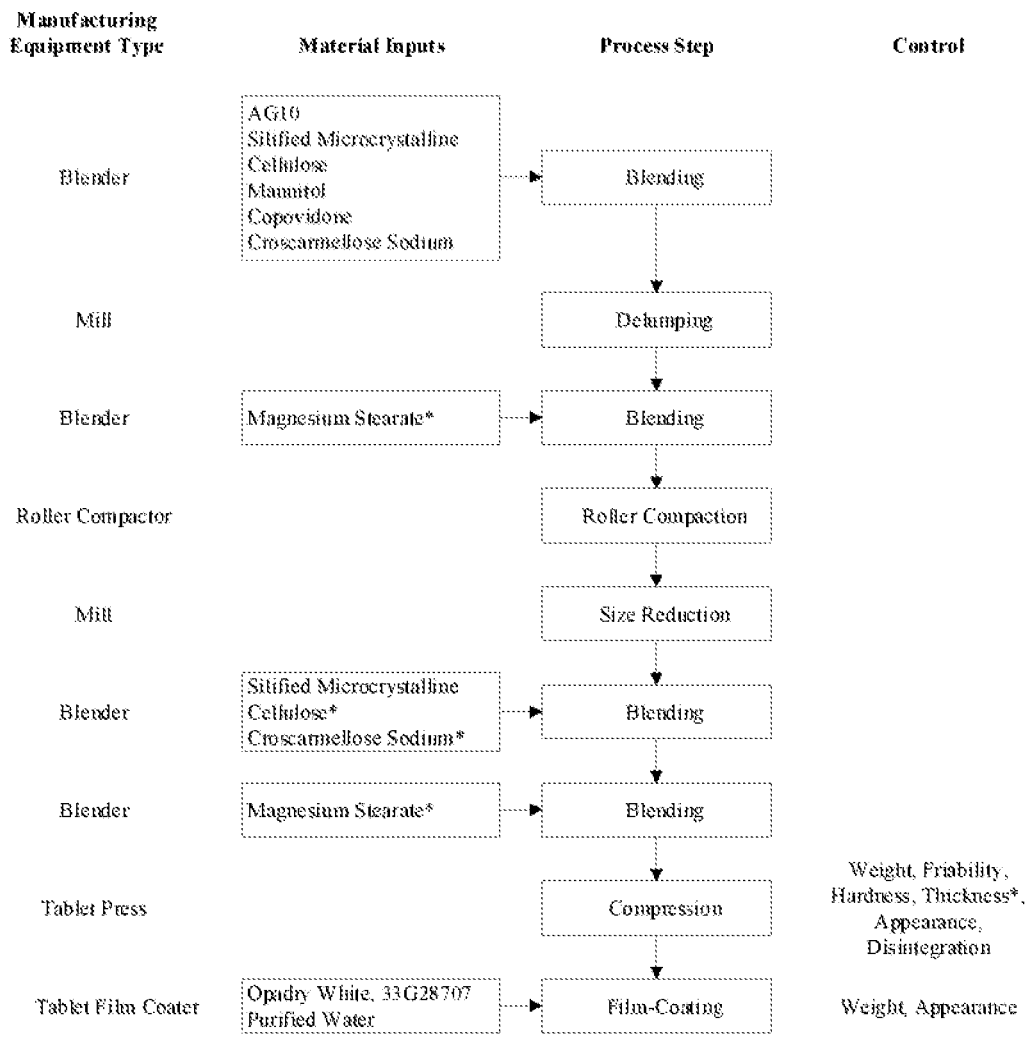
FIG. 8 illustrates the process Flow Diagram for the 33% AG10 HCl Tablets described in Example 4.
Figure 9:
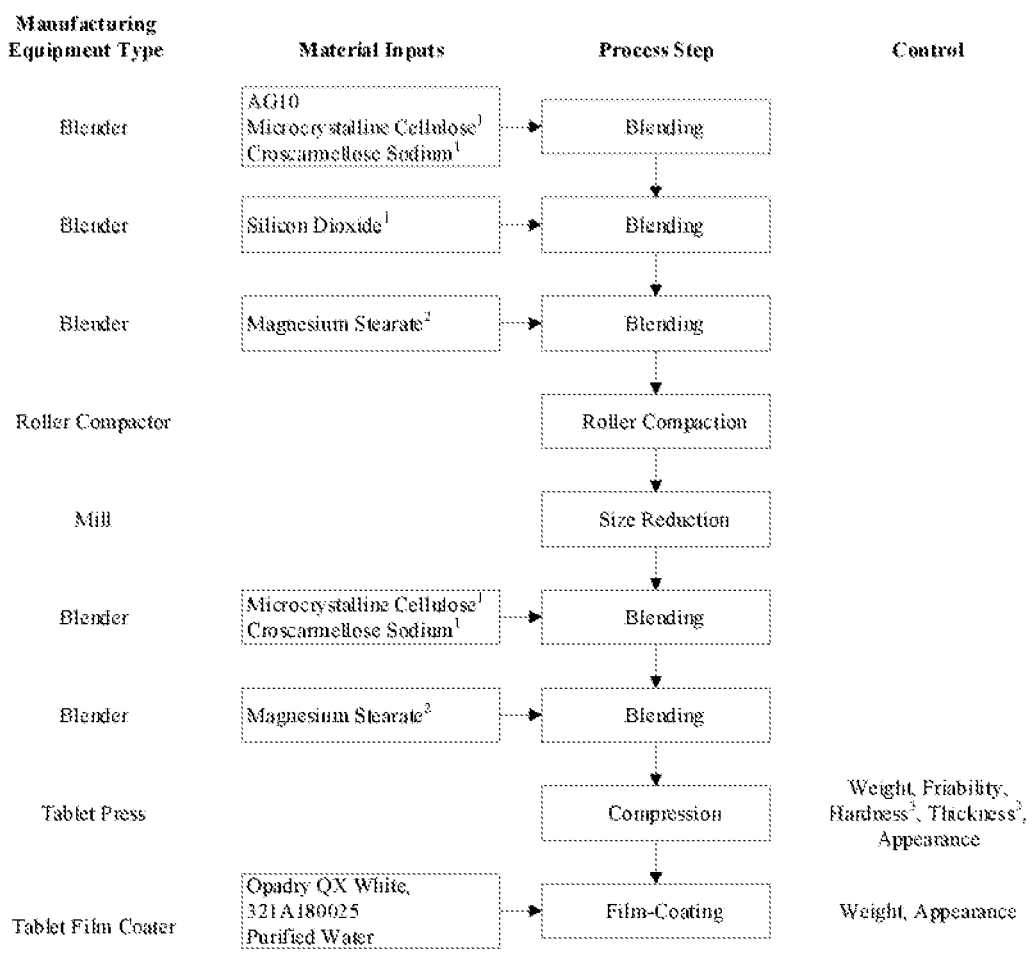
FIG. 9 illustrates the process Flow Diagram for the 66.7% AG10 HCl Tablets described in Example 4.

The manufacturing process for the two tablet formulations is shown in FIG. 8 and FIG. 9.

Figure 10:
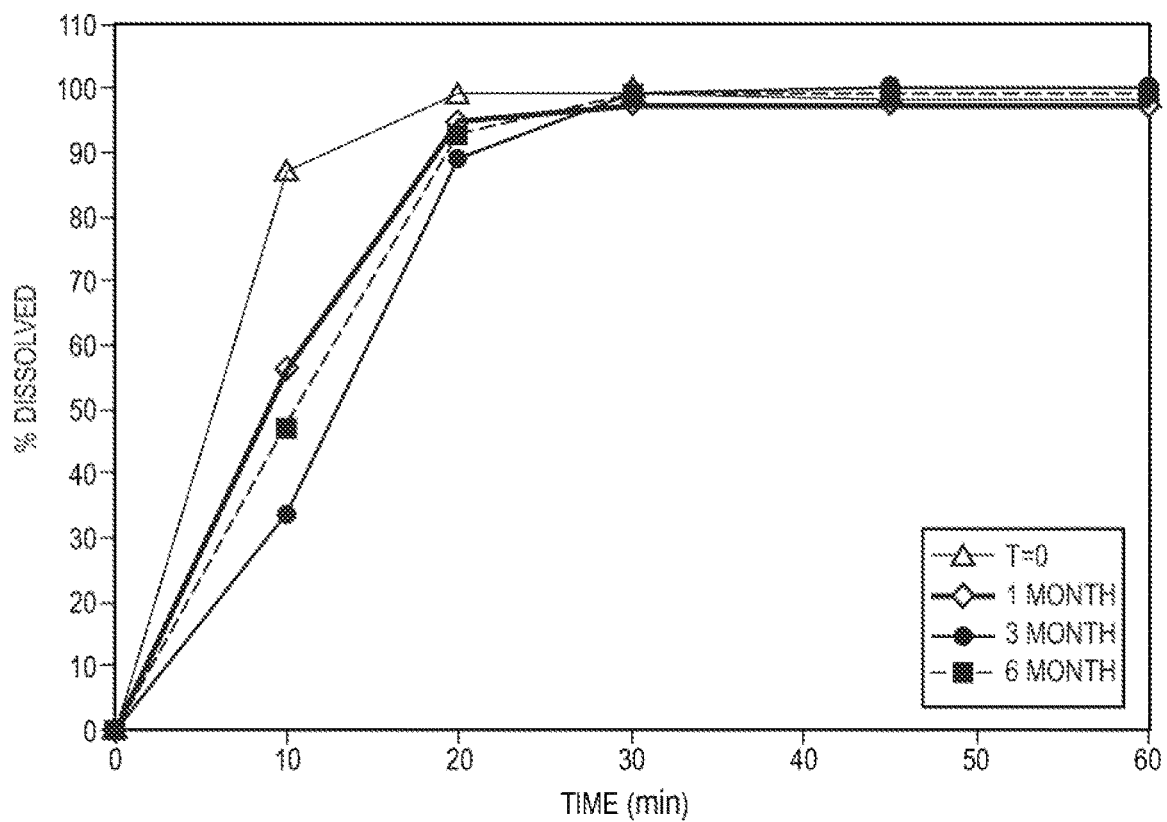
FIG. 10 shows the dissolution profile of 33.3% AG10 HCl tablets after storage under 40° C./75% RH Conditions. T=0 (open triangles); T=1 Month (open diamonds) T=3 Months (filled circles); T=6 months (filled squares).

33% AG10 HCl tablets were bottled and placed under accelerated storage (40° C./75% relative humidity (RH)) conditions. FIG. 10 shows that storage under accelerated storage conditions significantly reduced the dissolution rate of 33% AG10 HCl tablets.

Figure 11:
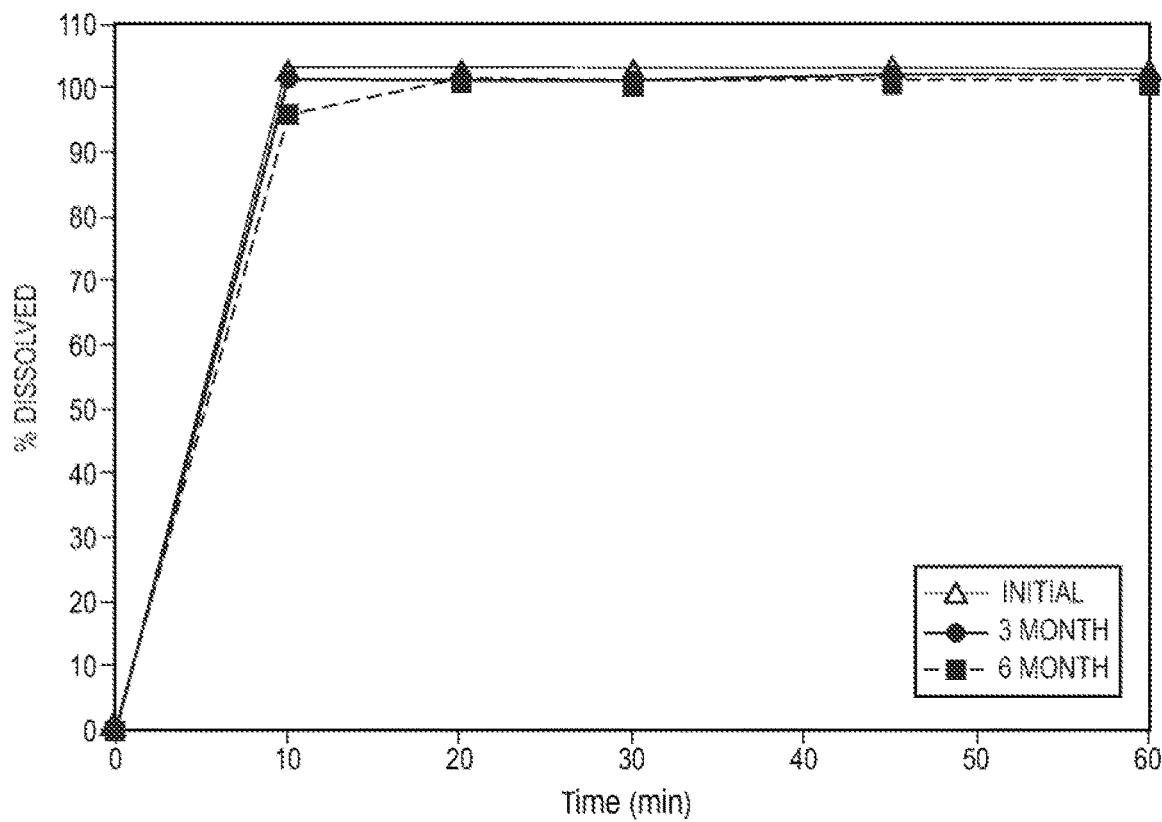
FIG. 11 shows the dissolution profile of 66.7% AG10 HCl tablets after storage under 40° C./75% RH Conditions. T=0 (open triangles); T=3 Months (filled circles); T=6 months (filled squares).

66.7% AG10 HCl tablets were also bottled and placed under accelerated storage conditions. FIG. 11 shows that 400 mg AG10 HCl tablets did not show a reduction in dissolution rate after storage for 6 months.

Both formulations of AG10 HCl tablets were evaluated using the same dissolution method (USP 2 Apparatus (Paddles), 900 mL 0.1 N HCl, 75 RPM, 37° C.) for release and for stability studies. The 66.7% AG10 HCl tablet formulation was superior relative to the 33% AG10 HCl tablet formulation in terms of dissolution rate after storage, indicating that the 66.7% AG10 HCl tablet has improved storage capacity.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A tablet formulation comprising AG10 or a pharmaceutically acceptable salt thereof and one or more fillers, one or more disintegrants, and one or more lubricants, wherein said tablet formulation comprises:
   40 to 85% by weight of AG10 or a pharmaceutically acceptable salt thereof;

5 to 55% by weight of said one or more fillers;

3 to 8% by weight of said one or more disintegrants; and 0.5 to 3% by weight of said one or more lubricants, and wherein said one or more fillers comprise a high-grade microcrystalline cellulose characterized by cellulose polymers with (i) spherical morphology and porous structure or (ii) needle-like particle shape.

2. The tablet formulation of claim 1, comprising about 50 to 75% by weight of AG10 or a pharmaceutically acceptable salt thereof.

3. The tablet formulation of claim 1, comprising about 50% by weight of AG10 or a pharmaceutically acceptable salt thereof.

4. The tablet formulation of claim 1, comprising about 66.7% by weight of AG10 or a pharmaceutically acceptable salt thereof.

5. The tablet formulation of claim 1, comprising about 75% by weight of AG10 or a pharmaceutically acceptable salt thereof.

6. The tablet formulation of claim 1, wherein said one or more fillers comprises about 10 to 50% by weight of said tablet formulation.

7. The tablet formulation of claim 1, wherein said one or more fillers comprises about 15 to 45% by weight of said tablet formulation.

8. The tablet formulation of claim 1, wherein said one or more fillers further comprise silicon dioxide.

9. The tablet formulation of claim 1, wherein said one or more disintegrants comprises about 6% by weight of said tablet formulation.

10. The tablet formulation of claim 1, wherein said one or more disintegrants is croscarmellose sodium.

11. The tablet formulation of claim 1, wherein said one or more lubricants comprises about 1.5% by weight of said tablet formulation.

12. The tablet formulation of claim 11, wherein said one or more lubricants comprise magnesium stearate.

13. The tablet formulation of claim 1, wherein said tablet formulation is at least 75% dissolved after performance of a dissolution test in a solution of 0.1N HCl at 37±0.5° C. in an Apparatus-II (Paddles) with a paddle speed of about 50 rpm for 10 minutes.

14. The tablet formulation of claim 13, wherein said tablet formulation is at least 85% dissolved after performance of said dissolution.

15. The tablet formulation of claim 14, wherein said tablet formulation is at least 95% dissolved after performance of said dissolution.

16. The tablet formulation of claim 13, wherein said dissolution test is performed at least three months after preparation of said tablet formulation.

17. The tablet formulation of claim 1, further comprising a coating agent.

18. The tablet formulation of claim 1, wherein AG10 is the pharmaceutically acceptable salt form of Formula Ia

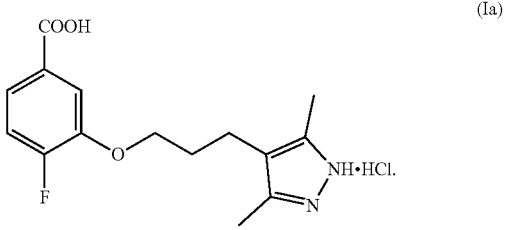

(Ia)

19. A method of treating transthyretin amyloid (ATTR) cardiomyopathy comprising administering a tablet formulation of claim 1.

20. A method of treating transthyretin amyloid (ATTR) polyneuropathy comprising administering a tablet formulation of claim 1.

21. The tablet formulation of claim 1, wherein said one or more fillers comprises about 25.8% by weight of said tablet formulation.

22. The tablet formulation of claim 1, wherein said one or more fillers comprises about 42.5% by weight of said tablet formulation.

23. A tablet formulation comprising AG10 or a pharmaceutically acceptable salt thereof and one or more fillers, one or more disintegrants, and one or more lubricants, wherein said tablet formulation comprises:

50 to 75% by weight of AG10 or a pharmaceutically acceptable salt thereof;

15 to 45% by weight of said one or more fillers;

3 to 8% by weight of said one or more disintegrants; and 0.5 to 3% by weight of said one or more lubricants, and wherein said one or more fillers comprise a high-grade microcrystalline cellulose characterized by cellulose polymers with (i) spherical morphology and porous structure or (ii) needle-like particle shape.

24. The tablet formulation of claim 23, wherein AG10 is the pharmaceutically acceptable salt form of Formula Ia

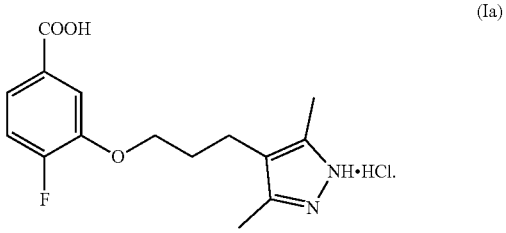

(Ia)

25. A method of treating transthyretin amyloid (ATTR) cardiomyopathy comprising administering a tablet formulation of claim 23.

26. A method of treating transthyretin amyloid (ATTR) polyneuropathy comprising administering a tablet formulation of claim 23.

* * * * *